(12) United States Patent
Chow et al.

(10) Patent No.: US 9,101,436 B2
(45) Date of Patent: Aug. 11, 2015

(54) DENTAL AND ENDODONTIC FILLING MATERIALS AND METHODS

(75) Inventors: Laurence C. Chow, Potomac, MD (US); Shozo Takagi, Gaithersburg, MD (US)

(73) Assignee: ADA FOUNDATION, Gaithersburg, MD (US)

( * ) Notice: Subject to any disclaimer, the term of this patent is extended or adjusted under 35 U.S.C. 154(b) by 262 days.

(21) Appl. No.: 11/550,543

(22) Filed: Oct. 18, 2006

(65) Prior Publication Data

US 2007/0092856 A1    Apr. 26, 2007

Related U.S. Application Data

(60) Provisional application No. 60/728,838, filed on Oct. 21, 2005, provisional application No. 60/728,888, filed on Oct. 21, 2005.

(51) Int. Cl.
*A61K 6/08* (2006.01)
*A61C 5/04* (2006.01)
*A61K 6/00* (2006.01)

(52) U.S. Cl.
CPC ............... *A61C 5/04* (2013.01); *A61K 6/0038* (2013.01)

(58) Field of Classification Search
CPC ...................................................... A61C 5/04
USPC ................... 424/434; 523/113, 114, 115, 116
See application file for complete search history.

(56) References Cited

U.S. PATENT DOCUMENTS 3,620,778 A * 11/1971 Morrell ..................... 523/109
4,182,829 A * 1/1980 Walkowiak et al. ......... 528/75
4,349,470 A    9/1982 Battista
4,357,165 A   11/1982 Helferich et al.
4,542,172 A    9/1985 Jochum et al.
4,612,053 A    9/1986 Brown et al.
4,664,857 A    5/1987 Nambu
4,902,649 A    2/1990 Kimura et al.

(Continued)

FOREIGN PATENT DOCUMENTS

DE    10021605    11/2001
EP     1384704     1/2004

(Continued)

OTHER PUBLICATIONS

Shimizu et al., Computer generated English translation of JP 06-287133 A, Oct. 11, 1994.*

(Continued)

*Primary Examiner* — Peter F Godenschwager
*Assistant Examiner* — David Karst
(74) *Attorney, Agent, or Firm* — Key IP Law Group, PLLC

(57) ABSTRACT

Disclosed are endodontic filling materials and methods. A method for filling a dental root canal may include providing a hydrosetting filling material and inserting the hydrosetting filling material into the dental root canal, the material setting in the root canal to form a biocompatible filling. The hydrosetting filling material comprises a hydrogel former and a filler. The hydrogel former is at least one of a reactive organic hydrogel formers, an inorganic hydrogel formers, and a non-reactive organic hydrogel formers, and the filler is at least one of a self-hardening and a non-hardening filler. Plural filling material precursor compositions that collectively contain hydrogel formers and fillers may be provided.

4 Claims, 1 Drawing Sheet

(56) References Cited

U.S. PATENT DOCUMENTS

| | | | |
|---|---|---|---|
| 5,092,888 A | | 3/1992 | Iwamoto et al. |
| 5,180,426 A | | 1/1993 | Sumita |
| 5,238,491 A | | 8/1993 | Sughihara et al. |
| 5,306,337 A | * | 4/1994 | Winkel et al. .................. 106/35 |
| 5,342,441 A | | 8/1994 | Mandai et al. |
| 5,409,703 A | | 4/1995 | McAnalley et al. |
| 5,415,547 A | | 5/1995 | Torabinejad et al. |
| 5,508,342 A | | 4/1996 | Antonucci et al. |
| 5,520,992 A | | 5/1996 | Douglas et al. |
| 5,769,638 A | * | 6/1998 | Torabinejad et al. ...... 433/228.1 |
| 5,900,254 A | | 5/1999 | Constantz |
| 5,955,096 A | * | 9/1999 | Santos et al. .................. 424/434 |
| 5,997,624 A | * | 12/1999 | Chow et al. ..................... 106/35 |
| 6,028,125 A | | 2/2000 | Combe et al. |
| 6,197,846 B1 | | 3/2001 | Combe et al. |
| 6,325,992 B1 | | 12/2001 | Chow et al. |
| 6,387,978 B2 | | 5/2002 | Ronan et al. |
| 6,472,454 B1 | | 10/2002 | Qian |
| 6,500,004 B2 | * | 12/2002 | Jensen et al. ............... 433/228.1 |
| 6,521,246 B2 | | 2/2003 | Sapieszko et al. |
| 6,559,200 B1 | * | 5/2003 | Kamohara et al. ............ 523/109 |
| 6,566,418 B2 | | 5/2003 | Imai et al. |
| 6,605,294 B2 | | 8/2003 | Sawhney et al. |
| 6,652,282 B2 | * | 11/2003 | Jensen et al. ............... 433/228.1 |
| 6,652,875 B1 | | 11/2003 | Bannister |
| 6,787,584 B2 | | 9/2004 | Jia et al. |
| 6,793,725 B2 | * | 9/2004 | Chow et al. ..................... 106/35 |
| 6,818,018 B1 | * | 11/2004 | Sawhney .................... 623/11.11 |
| 6,860,932 B2 | * | 3/2005 | Oshida ............................ 106/35 |
| 6,887,920 B2 | * | 5/2005 | Ohtsuki et al. ................ 523/116 |
| 6,905,516 B1 | | 6/2005 | Lemaitre et al. |
| 7,407,542 B2 | | 8/2008 | Lemaitre et al. |
| 2002/0045678 A1 | * | 4/2002 | Lopez et al. ................... 523/116 |
| 2003/0167093 A1 | | 9/2003 | Xu et al. |
| 2003/0199615 A1 | * | 10/2003 | Chaput et al. ...................... 524/2 |
| 2003/0232895 A1 | | 12/2003 | Omidian et al. |
| 2004/0009205 A1 | * | 1/2004 | Sawhney ....................... 424/423 |
| 2004/0097612 A1 | * | 5/2004 | Rosenberg et al. ........... 523/113 |
| 2004/0110863 A1 | * | 6/2004 | Zech et al. .................... 523/109 |
| 2004/0244651 A1 | | 12/2004 | Lemaitre et al. |
| 2006/0198863 A1 | | 9/2006 | DePaula |
| 2006/0213398 A1 | | 9/2006 | Barralet et al. |

FOREIGN PATENT DOCUMENTS

| | | | |
|---|---|---|---|
| GB | 1091476 A | * 11/1967 | ............. C08F 29/46 |
| JP | S58-208205 | 12/1983 | |
| JP | H02-034172 | 2/1990 | |
| JP | 2311406 | 12/1990 | |
| JP | 06287133 A | * 10/1994 | ............... A61K 9/06 |
| JP | H08-511964 | 12/1996 | |
| WO | WO 03041753 | 5/2003 | |

OTHER PUBLICATIONS

Shiozu, T., JP 02-311406 A English translation, Dec. 27, 1990.*
PCT International Search Report dated Aug. 8, 2007.
Brown and Chow, A New Calcium Phosphate Water Setting Cement, pp. 352-379 in Brown, Cements Research Progress, American Ceramic Society, OH, 1986.
Ginebra et al., Setting Reaction and Hardening of an Apatitic Calcium Phosphate Cement, J. Dent. Res. 76:905-912, 1997.
Constantz et al., Histological, Chemical, and Crystallographic Analysis of Four Calcium Phosphate Cements in Different Rabbit Osseous Sites, J Biomed Mater. Res. [Appl. Biomater.] 43:451-461, 1998.
Miyamoto et al., Histological and Compositional Evaluations of Three Types of Calcium Phosphate Cements When Implanted in Subcutaneous Tissue Immediately After Mixing, J. Biomed. Mater. Res. [Appl. Biomater.] 48:36-42, 1999.
Lee et al., Alpha-BSM(R): A Biomimetic Bone Substitute and Drug Delivery Vehicle, Clin. Orthop Rel. Res. 367:396-405, 1999.
Ishikawa et al., Reaction of Calcium Phosphate Cements with Different Amounts of Tetracalcium Phosphate and Dicalcium Phosphate Anhydrous, J. Biomed. Mater: Res. 46:504-510, 1999.
Matsuya et al., Effects of Mixing Ratio and Ph on the Reaction Between Ca4[PO4]2O and CaHPO4, J. Mater. Sci.: Mater. in Med. 11:305-311, 2000.
Takagi et al., Morphological and Phase Characterizations of Retrieved Calcium Phosphate Cement Implants, J. Biomed. Mater. Res. [Appl. Biomater.]58:36-41, 2001.
Shindo et al., Facial Skeletal Augmentation Using Hydroxyapatite Cement, Arch. Otolaryngol. Head Neck. Surg., 119:185-190, 1993).
Sugawara et al., In vitro Evaluation of the Sealing Ability of a Calcium Phosphate Cement When Used as a Root Canal Sealer-Filler, J. Endodont. 16:162-165, 1990).
Chohayeb et al., Evaluation of Calcium Phosphate as a Root Canal Sealer-Filler Material, J. Endodont. 13:384-387,1987.
Takagi et al., "Properties of premixed calcium phosphate cement pastes," J. Biomed Mater Res. [Applied Biomater] 67B:689-696 (2003).
Chow et al., "Rapid-Hardening, Pre-mixed Calcium phosphate cement pastes," Abs. No. 844, J. Dent. Res., Spec. Iss. A82 (2003).
Carey et al., "Premixed Rapid-Setting Calcium Phosphate Composites for Bone Repair," Biomaterials 24:5002-14 (2005).
Hauman C.H.J., Love R.M., Biocompatibility of Dental Materials Used in Contemporary Endodontic Therapy: A Review. Part 2 Root-Canal Filling Materials, Int. Endod. J. 36:147-160 (2003).
Frank, A., Therapy for the Divergent Pulpless Tooth by Continued Apical Formation, J. Am. Dent. Ass. 72:87-93 (1966).
Weisenseel J.A. et al., Calcium Hydroxide as an Apical Barrier, J. Endod. 13:1-5 (1987).
Schumacher J.W., Rutledge R.E., An Alternative to Apexification, J. Endod. 19:529-531 (1993).
Kratchman, S., Perforation Repair and One-Step Apexification Procedures, Dent. Clin. N. Am. 48 291-307 (2004).
Giuliani V. et al.: The Use of MTA in Teeth With Necrotic Pulps and Open Apices, Dent. Traumatol. 18(4):217-21 (2002).
Shabahang, S., Torabinejad, M., Treatment of Teeth With Open Apices Using Mineral Trioxide Aggregate, Pract. Periodont. Aesthe. Dent. 12(3):315-320 (2000).
PCT International Search Report dated Apr. 18, 2007.
Supplementary European Search Report of EP 06817258, dated May 5, 2011.
Examiner's first report on Australian patent application No. 2006304803, dated Jul. 26, 2011, pp. 1-3.
Japanese Office Action, Appln. No. 2008-536846, dated Jul. 3, 2012 (Translation of Notice of Reasons for Rejection is also attached).
USPTO Office Action mailed Nov. 28, 2012, U.S. Appl. No. 11/550,586.
Notice to File a Response (English translation of Korean Office Action) Application No. 10-2008-7012014 dated May 27, 2013, pp. 1-7.
U. Gbureck, S. Dembski, R. THull, J.E. Barralet, Factors influencing calcium phosphate cement shelf-life, Biomater, 2005, 26, p. 3691-3697.
USPTO Office Action mailed May 9, 2013, U.S. Appl. No. 11/550,586.

* cited by examiner

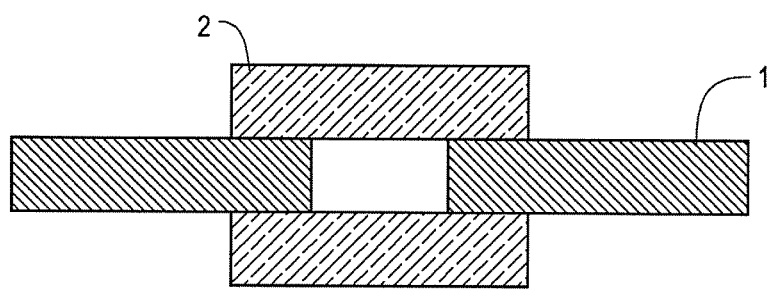

DENTAL AND ENDODONTIC FILLING MATERIALS AND METHODS

CROSS REFERENCE TO RELATED APPLICATION

This application claims priority to prior U.S. Provisional Application No. 60/728,838, the contents of which are incorporated by reference in their entireties. Additionally, this application contains subject matter that in some embodiments is related to some of the subject matter described in U.S. Provisional Application No. 60/728,888, filed Oct. 21, 2005, and entitled "Rapid Hardening Dual-Paste Premixed Calcium Phosphate Cements for Bone Defect Repair," and in U.S. patent application Ser. No. 11/550,586, entitled "Dual-Phase Cement Precursor Systems for Bone Repair," filed on the same day as the present application. These additional applications likewise are incorporated by reference in their entireties.

STATEMENT OF FEDERALLY SPONSORED RESEARCH

The invention was made in the course of research supported at least in part by Grant DE11789 from the National Institute of Dental and Craniofacial Research and carried out at the National Institute of Standards and Technology. The U.S. government may have certain rights to the invention.

TECHNICAL FIELD

This invention is in the field of dental and endodontic filling materials and methods.

BACKGROUND OF THE INVENTION

The root canal is a channel in the tooth that runs from the crown to the root in a normal tooth and that contains pulp, which is composed of connective tissue, nerves, and blood vessels. If the pulp is damaged by disease, trauma, or invasion of decay, a root canal treatment is recommended to avoid tooth loss. Treatment typically involves removal of irritants, necrotic tissue, and infected material from the root canal, enlarging and sanitizing the canal, and finally the sealing the canal. The sealing generally is followed with a post canal treatment such as a crown.

In such endodontic treatment, sealers and filling materials are sometimes placed directly on or against vital tissues. Accordingly, it is highly desirable that a material that is used for such a filling or sealing purpose be highly biocompatible. Currently, zinc oxide-eugenol, glass ionomers, amalgams, composite resins, and mineral trioxide aggregates (MTA) are used for root-end and perforation repair. Of these, MTA is currently thought to be one of the more biocompatible materials; see Hauman C. H. J., Love R. M., Biocompatibility Of Dental Materials Used In Contemporary Endodontic Therapy: A Review. Part 2 Root-Canal Filling Materials, *Int. Endod. J.* 36:147-160 (2003).

Apexification is an endodermic procedure that is related to the root canal procedure. In the apexification, a non-vital tooth with an open apex is filled with an interim filling material to control infection and to enable closure of the apex so that a definitive root canal treatment can be formed at a later time. Calcium hydroxide historically has been used to establish apical closure and to avoid surgery in the apexification procedure; see Frank, A., Therapy For The Divergent Pulpless Tooth By Continued Apical Formation, *J. Am. Dent. Ass.* 72:87-93 (1966). Calcium hydroxide is effective, but requires high patient compliance and multiple appointments extending over a long period of time. Additionally, in connection with calcium hydroxide treatment, susceptibility to coronal leakage and fracture of the root has been reported; see Weisenseel J. A. et al., Calcium Hydroxide As An Apical Barrier, *J. Endod.* 13:1-5 (1987) and Schumacher J. W., Rutledge R. E., An Alternative To Apexification, *J. Endod.* 19:529-531 (1993). A number of studies demonstrate that MTA is effective in apexification procedures; see Kratchman, S., Perforation Repair And One-Step Apexification Procedures, *Dent. Clin. N. Am.* 48 291-307 (2004); Giuliani V. et al.: The Use Of MTA In Teeth With Necrotic Pulps And Open Apices, *Dent. Traumatol.* 18(4):217-21 (2002); Shabahang, S., Torabinejad, M., Treatment Of Teeth With Open Apices Using Mineral Trioxide Aggregate, *Pract. Periodont. Aesthe. Dent.* 12(3): 315-320 (2000). MTA, however, has poor handling properties relative to calcium hydroxide, including long hardening times and a consistency that some deem too dry for delivery by injection.

The invention seeks, in certain embodiments, to provide endodontic materials and methods useful for root canal and/or apexification procedures.

SUMMARY OF THE INVENTION

Generally, endodontic materials and methods are provided. The endodontic materials are single-paste hydrosetting filling materials or plural-paste filling material precursor compositions. When in the form of a single-paste material, the material comprises a hydrogel former and a filler, the hydrogel former in some embodiments being at least one of a reactive organic hydrogel former, an inorganic hydrogel former, and a non-reactive hydrogel former, and the filler in some embodiments being at least one of a self-hardening and a non-hardening filler. The filling material may be formed in situ in the root canal, or just prior to insertion into the root canal, from plural precursor compositions. In accordance with these embodiments, at least first and second filling material precursors, upon blending and prior to setting, contain a hydrogel material and a filler. The hydrogel material is a hydrogel former as described above, and optionally a stable hydrogel, and similarly, the filler is one or both of a self-hardening and non-hardening filler as discussed hereinabove. Endodontic methods and kits likewise are contemplated in one or more of the various embodiments of the invention.

BRIEF DESCRIPTION OF THE DRAWING

The FIGURE is a side elevational view of a mold in which the endodontic materials described in certain Examples were evaluated.

DETAILED DESCRIPTION OF CERTAIN EMBODIMENTS

In some embodiments, the invention is directed towards an endodontic filling material. It is contemplated that the filling material may be used in lieu of conventional filling materials, such as gutta percha, with a suitable separate sealer, such as any conventional sealer known in the art. Alternatively, it is contemplated that the filling material may be used as a single endodontic filling material, without the need for a separate sealer. Generally, it is contemplated that a superior tooth treatment, such as a post or crown, will be used to complete the tooth restorative efforts, although it is also contemplated that in some instances no superior tooth treatment is employed. In many cases, it is contemplated that the materials are of such consistency and viscosity that they can be delivered to the root canal by injection, possibly with the assistance of a heating step.

A number of properties are desired for endodontic materials, and it is contemplated in many embodiments that the materials used in conjunction with the claimed invention will satisfy most or all of these properties. Specifically, it is desired that the endodontic material be highly biocompatible, by which is contemplated compatibility with both soft and hard tissues. Desirably, no chronic inflammatory tissue response is observed using the materials. The materials should be resistant to leakage, and should provide a high level of sealing ability against the penetration of bacteria and bacterial products. For similar reasons, the materials themselves in many cases are highly alkaline, such that they are able to neutralize the acid products of bacteria or of inflamed cells. Alkaline material may be incorporated as part of the filler in the filling material; alternatively, in some embodiments, a separate antibacterial component may be employed. The filling materials should be insoluble in normal physiological environments and under locally acidic conditions that may result upon exposure to bacteria or inflamed cells. The materials should be stable and resistant to washout in the root canal.

The endodontic materials generally are contemplated to set to form a filled hydrogel filling. Without intending to limit the invention to a particular theory of operation, the hydrogel is believed to serve as a cohesive and washout-resistant matrix for holding the filler particles in place, thereby providing a stable mass for filling and sealing the root canal. For certain reactive fillers, the hydrogel serves as an aqueous matrix to allow the fillers to take the form of a hardened mass. Similarly, the hydrogel is believed to provide leakage resistance by filling pores that ordinarily would otherwise be present in the filling material. Without intending to limit the invention to a particular theory of operation, the fillers are believed to provide bulk and mechanical strength, thereby allowing the filling the material to be solid and stiff. Fillers provide leakage resistance and alkalinity, and can provide radio opacity. For certain reactive hydrogels, the filler provides ionic calcium and/or alkalinity needed to react with polymers. Similarly, the filler is insoluble in the locally acidic environment resulting from production of acid by bacteria or inflamed cells.

As heretofore stated, the filling materials may take the form of single-paste filling materials or plural-paste filling materials. The term "paste" is not intended to be limiting or to necessarily connote any adhesive properties other than those stated. When in the form of a single paste filling material, the filling material should include a hydrogel former and a filler. Any suitable hydrogel former and filler may be used in conjunction with the invention. In many embodiments, the hydrogel former includes a reactive organic hydrogel former, a non-reactive organic hydrogel former, or an inorganic hydrogel former. These embodiments are not mutually exclusive, and it is contemplated in some embodiments that plural types of hydrogel formers are included.

When an inorganic hydrogel former or a reactive organic hydrogel former is employed, generally the filling material will be non-aqueous, by which is contemplated the complete or substantial absence of water to the extent practicable, or the absence of water to the extent sufficient to provide a filling material that is stable prior to introduction into a root canal. The inorganic or reactive organic hydrogel former may be disposed in a non-aqueous liquid carrier. In such embodiments, after the material is placed into the root canal, water from surrounding tissue gradually replaced the non-aqueous liquid carrier, thereby allowing the reactive organic hydrogel former or the inorganic hydrogel former to form a hydrogel. In some cases, chemical reactions also occur between the hydrogel former and the filler when the environment becomes aqueous, thus forming a hardened hydrogel.

Exemplary organic hydrogel formers include chitosans and biocompatible derivatives thereof which are believed to form a hydrogel by settling out of liquid phase due to an increase in pH produced by the dissolution of fillers in an aqueous environment. Other hydrogel formers include alginates and pectinates, such as sodium alginate and sodium pectinate, which form a gel by cross-linking with calcium derived from the dissolution of soluble calcium-contained fillers in aqueous environment; and polyacrylic, poly-itaconic, or other poly-alkenoic acids or copolymers thereof, the hardening of which generally requires a base and calcium. The pectinates or alginates may be derived from pectinic and alginic acids. The liquid carrier may be any suitable non-aqueous material such as ethanol, propanol, glycerol, certain polyethylene glycols, and propylene glycol, these materials being liquid at 25° C. Exemplary inorganic hydrogel formers include tricalcium silicate, dicalcium silicate, and sodium silicate.

Alternatively, or in addition thereto, the filling material may include a non-reactive organic hydrogel former. Generally, such materials comprise polymers that are blended in a non-aqueous liquid, such as those hereinbefore described. After introduction into a root canal, the non-aqueous liquid is gradually replaced by water that migrates from surrounding tissues. The polymer thus forms a hydrogel, but may not undergo a chemical reaction with the fillers. Exemplary non-reactive organic hydrogel formers include polyvinyl acetate, polyvinyl butyral, polyvinyl alcohols, hydroxymethyl cellulose, and konjac.

Mixtures of the foregoing types of hydrogel formers may be employed. In other embodiments, the paste may include a formed hydrogel. In some such embodiments, it may be desirable to heat the hydrogel to assist in transferring the filling material into a root canal, or to use mechanical assistance.

The filling material generally further includes a filler. Any suitable filler may be used in conjunction with the invention. In many embodiments, a self-hardening filler or non-hardening filler is employed. These embodiments are not mutually exclusive, and it is contemplated in some instances that both a self-hardening and a non-hardening filler may be employed.

Self-hardening fillers are those filling materials that do not harden in a non-aqueous environment, thereby allowing the filling material to remain soft and malleable in the provided package. These materials will, however, harden after being placed into a root canal, upon migration of water from surrounding tissues. Additionally, the self-hardening fillers may further react with the hydrogels by providing ionic calcium, or alkalinity, or both. Exemplary self-hardening fillers are the various self-setting calcium phosphate cements that have been reported in the scientific and patent literature, mineral trioxide aggregate (MTA), Portland cement, calcium silicates, and gypsum.

Non-hardening fillers are contemplated to include those fillers that, in the absence of hydrogel former, do not harden readily upon exposure to water. Such fillers may react with a reactive hydrogel after the material is placed into the root canal by providing calcium or alkalinity as needed to cause the hydrogel former to form a hydrogel. Exemplary non-hardening fillers include hydroxyapatite, fluorapatite, tricalcium phosphate, calcium oxide, barium sulfate, bismuth sulfate, calcium hydroxide, calcium fluoride, calcium silicate, calcium gluconate, calcium glycerophosphate, tetracalcium phosphate, and calcium aluminate. For those hydrogel formers that form hydrogels with calcium, calcium fillers, such as the heretofore mentioned calcium compounds, calcium chloride, and calcium acetate, may be employed. Generally, whether a self-hardening or non-hardening filler is employed, the filler should be selected to be consistent with the hydrogel former employed in the filling material. For instance, when a chitosan hydrogel former is employed, the filling material should include an alkaline species. Similarly, when a pectinate is employed, the filling material should include calcium. Those of skill in the art will recognize the various workable combinations of hydrogel formers and fillers that are suitable for use and conjunction with the invention.

The filling material may include other suitable ingredients. For instance, one or more radio opaque fillers may be employed. The radio opaque filler may, for instance, be a suitable bismuth, barium, or iodide compound, such as barium sulfate or bismuth hydroxide. Additionally, other fillers in addition to those heretofore described may be employed. The filling material may include components that modify the physical properties of the material, such as viscosity modifying agents. In some embodiments, the filling material may include medicaments or antibacterial agents, it being noted that some of the fillers are alkaline and possess antibacterial properties. Other suitable antibacterial components include eugenol, iodide materials, and other biocompatible components with antibacterial properties. When a calcium silicate compound is employed, excess calcium silicate beyond that needed for the hydrogel may function to an extent as a filler.

The filling material may be prepared from plural filling material precursor compositions, by which is contemplated that two or more precursor compositions, upon blending, form a filling material. The various components may be present in any suitable amounts relative to one another. For instance, in some embodiments, the hydrogel former is present in an amount of 5-85% by weight, or in some cases 20-66%. The filler may, in some embodiments, be present in an amount of 15-95% by weight, and in some cases 34-80%.

When in the form of plural pastes, generally, the filling material is formed by blending the precursors in situ in the root canal or immediately prior to application to the root canal. Each of the pastes may be aqueous or at least substantially non-aqueous, as discussed hereinabove. In some embodiments, one of the pastes is aqueous and the other one of the pastes is non-aqueous. When aqueous, the aqueous carrier may be water, saline, or, more generally, any suitable aqueous carrier. In still further embodiments, more than two precursor pastes are employed, although more than two pastes may not be necessary in many embodiments. The filling material precursor pastes form a filling material when mixed, the filing material containing a hydrogel former and filler as discussed hereinabove. Generally, it is contemplated that reactive organic hydrogel formers, non-reactive organic hydrogel formers, and inorganic hydrogel formers, and mixtures thereof, may be employed in connection with the plural paste embodiments of the invention. It is also contemplated that at least one of the pastes may include a formed hydrogel. Similarly, it is contemplated that self-hardening fillers and non-hardening fillers may be used in conjunction with these embodiments of the invention. The self-hardening filler may comprise plural components that harden upon introduction to one another; in these embodiments, one of the components may be present in one of the precursor pastes and the other component may be present in another precursor paste.

As with the single-paste filling materials, any one of the precursor pastes may contain additional components such as those described hereinabove, including materials such as radio opaque fillers (barium and bismuth sulfate being examples of such fillers), other fillers, antibacterial components, and components for modification of viscosity or other physical properties. Similarly, the amounts of hydrogel and filler may be present in any suitable amounts in each paste relative to one another. Generally, if a non-aqueous paste is employed, the hydrogel and filler may in some embodiments be present in amounts similar to those of the single-paste embodiments. For an aqueous paste, the hydrogel may be present in an amount of at least 5%, inclusive of water, and the filler may be present in any suitable amount, such as the balance of weight of the paste.

In some embodiments, the filling material, whether provided in the form of a single-paste filling material or a multiple-paste filling material precursor system, may be provided in the form of a kit. When a dual-paste system is employed, the kit may include the two pastes and separate containers suitable to maintain the pastes separately. In either case, the kit may include a tool for introducing the filling material to a root canal. The tool may comprise, for instance, a conventional syringe. When multiple pastes are employed, a microdispenser with a mixing tip, the mixing tip comprising an auger-like structure that allows the two pastes to be blended rapidly and subsequently to be applied to the desired area, may be employed. An example of such a device is the Dual-Barrel 9 ml Micro Dispensing System by Tah Industries, Robbinsville, N.J. The invention contemplates the use of this device, or an analogous device that is specifically designed for medial usage. In some embodiments, the micro dispensers may include a region that serves as the container for the pastes, by providing separate holding chambers for the first and second pastes.

Each paste preferably is sufficiently stable to permit transport and reasonable storage prior to use. Stability may be measured by any technique or using any criteria deemed appropriate. In accordance with one such technique, a sample of the material or materials constituting the paste or pastes is heated to a temperature of 50° C., and held at this temperature for seven days. The material then is used in the formation of a filling material, and the setting time of the material is evaluated as compared with the original setting time of a similar filling material made without thermal treatment. If the setting time of the filling material made with the thermally treated phase is approximately equal to the setting time of the similar filling material, the paste may be deemed suitably stable for use in conjunction with the present invention. The invention is not limited to pastes that meet this criterion; rather, the foregoing is provided to illustrate one of but many possible methods for evaluating stability.

As heretofore described, in use, the filling materials may be employed in endodontic and specifically apexification procedures. The filling material may be placed into a root canal, and optionally sealed with a secondary sealer. When the filling material is formed from plural precursor pastes, the pastes may be injected or otherwise introduced simultaneously into the root canal, or blended immediately prior to insertion into the root canal. In various embodiments, the material is useful generally as an endodontic material, as a filler or core, or sealer, as a material for retrofilling of root ends, for root canal perforation repairs, and in apexification procedures.

The following non-limiting Examples are provided to illustrate the invention.

Examples 1-19 describe premixed hydrogel pastes.

Example 1

A hydrogel phase was prepared by blending 0.3 grams of chitosan malate (Vanson, Redmond, Wash., USA) with 1.2 grams of glycerol. The filler phase was composed of 3 grams of Portland cement (the ingredient of mineral trioxide aggregates, also known as MTA) and 0.3 grams of calcium oxide (CaO). The hydrogel and the fillers were then thoroughly mixed to form a filling material, and this filling material was stored in an airtight vial.

An aliquot of approximately 0.3 grams of the premixed filling material was placed into a cylindrical mold 1 (6 mm D×3 mm H). The top and bottom faces of the mold were covered with fritted glass plates 2, as depicted in the FIGURE, and the assembly was placed in a 37° C. water bath to allow ingress of water into and egress of glycerol from the sample. Diffusion of water into the sample allowed Portland cement to dissolve, leading to an increase in the pH. The pH increase caused the chitosan to settle out of the solution and to form a hard, rubber-like elastomeric gel. The sample set within 20 minute and was demolded. The initial setting of the sample was caused by the hardening of the chitosan. The Portland cement in the filler phase hardened in about 1 to 2 hours. The sample then was allowed to set fully by placing it into water at 37° C. for an additional 24 hours.

The fully set sample then was subjected to a dye penetration test. The sample was placed in 5 mL of a 1% poly-R (Sigma Chemical, St Louis, Mo.) solution whose pH was adjusted to 7.4, and held at 37° C. for 3 days. Dye penetration into the sample, measured on fractured sample surfaces under an optical microscope (25×), was 0.11 mm±0.11 mm (mean±s.d.; n=6).

The filling material of this Example may take the form of a prepackaged product that hardens rapidly after is placed in a root canal, where the moisture in the tissue will initiate the setting. This filling material is significantly better than MTA-based filling materials currently available for endodontic treatments. It is highly cohesive and therefore can be easily placed into the root canal, and it sets much faster than conventional MTA-based filling materials.

Example 2

A hydrogel phase was prepared by blending 0.8 grams of chitosan malate (Vanson, Redmond, Wash., USA) with 1.2 grams of glycerol. The filler phase was composed of 1.5 grams of fluorapatite and 1.5 grams of CaO. The hydrogel and the fillers were then thoroughly mixed and stored in an airtight vial. An aliquot of approximately 0.3 grams of the premixed material was placed in a cylindrical mold and into a water bath as described in Example 1. Diffusion of water into the sample allowed CaO to dissolve, leading to an increase in the pH. The increased pH caused the chitosan to settle out of the solution, forming a hard gel. The sample set within 15 minute and was demolded. The sample was allowed to fully set by placing it into water at 37° C. for an additional 24 hours, and was then subjected to a dye penetration test as described above. Dye penetration into the sample was 0.38 mm±0.17 mm (mean±s.d.; n=6).

Although the fillers did not harden, the material had a hard, rubber-like consistency, and was chemically and dimensionally stable. The cement of this Example can be used as a prepackaged product that hardens rapidly after it is placed in a root canal, where the moisture in the tissue will initiate setting. This material is significantly better than many currently available endodontic materials treatments because it is highly biocompatible, it is cohesive, and it sets rapidly.

Example 3

The hydrogel phase was prepared by blending 0.2 grams of konjac Glucomannan powder (Konjac Foods, Sunnyvale, Calif.) with 0.8 grams of glycerol. The filler phase was composed of 2 grams of a self-hardening calcium phosphate cement (CPC) powder that included 72.6% tetracalcium phosphate and 27.4% dicalcium phosphate anhydrous. The hydrogel and the fillers were then thoroughly mixed and stored in an airtight vial. An aliquot of approximately 0.3 grams of the premixed material was placed in a cylindrical mold and the assembly placed in a water bath as in Example 1. The sample set within 2 hours and was demolded. The sample was allowed to fully set by placing it into water at 37° C. for an additional 24 hours and was then subjected to a dye penetration test as described above. Dye penetration into the sample was 0.38 mm±0.17 mm (mean±s.d.; n=6). This material also is an excellent endodontic filling material.

Example 4

A non-reactive hydrogel was prepared by blending 0.1 grams of polyvinylbutyral powder (mw=88,000, Scientific Polymer Products, Inc., Ontario, N.J.) with 0.4 grams of n-propyl alcohol (Mallinckrodt). The filler phase contained 1 gram of a self-hardening calcium phosphate cement (CPC) powder that was composed of 72.6% tetracalcium phosphate and 27.4% dicalcium phosphate anhydrous, 0.25 grams of ground tetracalcium phosphate, and 0.25 grams of $Ca_3SiO_5$. The hydrogel and the fillers were thoroughly mixed and stored in an airtight vial. A mold was prepared and subjected to a dye penetration test as described above. Dye penetration into the sample was 0.04 mm±0.03 mm (mean±s.d.; n=5). In this example, $Ca_3SiO_5$ primarily plays the role of a filler that provides alkalinity.

Examples 5-7

A non-reactive hydrogel containing 0.5 grams of polyvinylbutyral powder (mw=88,000, Scientific Polymer Products, Inc., Ontario, N.J.) dissolved in 1.5 grams of absolute ethanol was provided. A premixed paste was prepared by mixing the hydrogel and a Portland cement powdered filler thoroughly at a ratio (g/g) (P/L) of 3. A mold was prepared and bathed as described above. The sample was demolded after 4 hours and was placed into water at 37° C. for an additional 20 h, and subsequently subjected to a dye penetration test as described above. Seven-day dye penetration into the sample was 0.05 mm (n=5).

Samples were also prepared using P/L=2 (Example 6) and 1 (Example 7). In these cases, the dye penetration were 0.08 mm and 0.63 mm (n=5), respectively.

Examples 8-10

A non-reactive hydrogel was prepared by dissolving 0.2 grams of polyvinylbutyral powder (mw=88,000, Scientific Polymer Products, Inc., Ontario, N.J.) in 1.8 grams of absolute ethanol. A premixed paste was prepared by mixing the hydrogel and a Portland cement powdered filler thoroughly at a ratio (g/g) (P/L) of 3. The paste was molded and bathed as described above. The sample was demolded after 4 hours and placed into water at 37° C. for an additional 20 h It was subjected to a dye penetration test as described above. Seven-day dye penetration into the sample was 0.03 mm (n=5). The test was repeated, except that the samples were held for 37° C. for one week. No significant difference in test results was observed.

Samples were also prepared using P/L=2 (Example 9) and 1 (Example 10). In these cases, the dye penetration were 0.09 mm and 0.44 mm (n=5), respectively.

Example 11

A non-reactive hydrogel was prepared by blending 2.5 grams of polyvinyl acetate powder (PVAc) (mw=45,000, Polysciences, Inc., Warrington, Pa.) with 7.5 mL of absolute ethanol. A non-hardening filler phase that was composed of 2 grams of fluorapatite (FA) (General Electric Company, Cleveland, Ohio) and 1 grams of CaO (Fisher Scientific, Fair Lawn, N.J.) was prepared. The hydrogel and the fillers were thoroughly mixed and stored in an airtight vial. The material was molded and bathed as described above, then demolded after 18 hours and placed into water at 37° C. for an additional 48 hours. The molded filler material was observed to be slightly swelled. Dye penetration into the sample was 0.18 mm±0.09 mm (mean±s.d.; n=6). For this and the following Examples, the samples were in the dye solution for at least three days, sometimes three to five days.

Example 12-19

The following Examples were performed, and dye penetration results were observed. The hydrogels in these Examples were prepared as described above.

| Example | Hydrogel | Fillers | Dye Penetration[1] |
|---|---|---|---|
|  | Control - 1 g glycerol (without polymer) | 2.2 g $Ca_4(PO_4)_2O$ + 0.8 g $CaHPO_4$ | >1.5 |
| 12 | 1.6 g chitosan malate + 2.4 g glycerol | 1.5 g $CPC^2$ + 1.5 g CaO | 0.38 ± 0.24 |
| 13 | 0.1 g Na alginate + 0.9 g glycerol | 3.2 g CPC + 1 g CaO | 0.10 ± 0.08 |
| 14 | $PVAc^3$ + ethanol[4] | 3 g CPC | 0.07 ± 0.01 |
| 15 | 0.375 g $PVB^5$ + 1.125 g ethanol | 3 g Portland cement | 0.02 ± 0.03 |
| 16 | 0.25 PVB + 0.75 g ethanol | 2 g CPC + 1 g CaO | 0.35 ± 0.20 |
| 17 | 0.385 g $PAAc^6$ + 1.155 g water | 3 g CPC | 0.16 ± 0.08 |
| 18 | 0.1 g $PVB^5$ + 0.4 g ethanol | 1.5 g CPC + 0.1 g $Na_3PO_4 \cdot 12H_2O$ | 0.26 ± 0.08 |
| 19 | 0.1 g $PVB^5$ + 0.4 g ethanol | 1 g CPC + 0.5 g TTCP + 0.15 g $Na_3PO_4 \cdot 12H_2O$ | 0.13 ± 0.05 |

[1] values are in mm (mean ± s.d.; n = 6)
[2] CPC was composed of 72.6% tetracalcium phosphate and 27.4% dicalcium phosphate anhydrous
[3] polyvinyl acetate (mw = 45,000, Polysciences Inc., Warrington, PA)
[4] water free ethanol (200 proof)
[5] polyvynylbutyral (mw = 88,000, Scientific Polymer Products, Inc., Ontario, NJ)
[6] polyacrylic acid (mw = 240,000) came with liquid (25%) (Aldrich Chemical Company, Inc., Milwaukee, WI).

Examples 20-33 describe two-paste systems.

Example 20

A non-aqueous paste that contained 0.6 grams of chitosan malate in 0.9 grams of glycerol as a reactive hydrogel precursor and 3 grams of Portland cement as a self-hardening filler system was provided. Also provided was an aqueous paste that contained 0.05 grams of poly vinyl alcohol (PVA) dissolved in 0.45 grams of water as a non-reactive hydrogel and 2 grams of fluorapatite (FA) as a non-hardening filler. Upon combination of the two pastes, chitosan malate dissolved in the water and formed a hardened gel within 7 min with the aid of base derived from Portland cement. Additionally, the water from the aqueous phased allowed Portland cement to harden. Because water was provided by one of the pastes, the mold described above was not used. For setting time measurement in this and the following two-paste examples, the mixed paste was placed into a stainless steel mold (6 mm d×3 mm high) that was covered with two regular glass plates and left in 100% humidity air at 37° C. The sample was allowed to fully set by placing it into water at 37° C. for an additional 24 hours and was then subjected to a dye penetration test as described above. Dye penetration into the sample was 0.31 mm±0.09 mm (mean±s.d.; n=6).

Example 21

A non-aqueous paste that contained 0.6 grams of chitosan malate in 0.9 grams of glycerol as a reactive hydrogel precursor and 2 grams of tetracalcium phosphate (TTCP) as an incomplete portion of a self-hardening (TTCP+DCPA) calcium phosphate cement filler system was provided. Also provided was an aqueous paste that contained 0.056 grams of PVA dissolved in 0.5 grams of water as a non-reactive hydrogel and 1 gram of dicalcium phosphate anhydrous (DCPA) as the other portion of the calcium phosphate cement filler system. Once the two pastes were combined, chitosan lactate dissolved in the water and formed a hardened gel within 15 min with the aid of base derived from TTCP. Additionally, the TTCP and DCPA react to form hardened cement with hydroxyapatite as the product. The sample was molded as described above, and was allowed to fully set by placing it into water at 37° C. for an additional 24 hours and was then subjected to a dye penetration test as described above. Dye penetration into the sample was 0.17 mm±0.10 mm (mean±s.d.; n=6).

Example 22

In this Example, the non-aqueous paste contained 0.6 grams of chitosan malate in 0.9 grams of glycerol as a reactive hydrogel precursor and 2 grams of FA as a non-hardening filler. The aqueous paste contained 0.1 grams of PVA dissolved in 0.9 grams of water as a non-reactive hydrogel and 2 grams of TTCP as a non-reactive filler. The two pastes were combined and allowed to set, then allowed to fully set by placing it into water at 37° C. for an additional 24 hours. Dye penetration into the sample was 0.35 mm±0.08 mm (mean±s.d.; n=6).

Example 23

In this Example, the non-aqueous paste contained 0.6 grams of chitosan malate in 0.9 grams of glycerol as a reactive hydrogel precursor, 2.5 grams of Portland cement as a self-hardening filler system, and 0.5 grams of calcium chloride as a soluble calcium source. The aqueous paste contained 0.2 grams of sodium alginate in 0.8 grams of water as a reactive hydrogel and 1 gram of FA as a non-hardening filler. Once the two pastes were combined, the paste hardened within 10 minute. The hardening mechanisms included (1) chitosan malate dissolved in the water and formed a hardened gel with the aid of base derived from Portland cement, (2) the alginate gel hardened by cross linking with the calcium from the calcium chloride originally present in the non-aqueous paste, and (3) the water from the aqueous allowed Portland cement to harden. The sample was allowed to fully set by placing it into water at 37° C. for an additional 24 hours and was then subjected to a dye penetration test as described above. Dye penetration into the sample was 0.35 mm±0.07 mm (mean±s.d.; n=6).

Example 24

In this Example, the non-aqueous pastes contained 0.1 grams of sodium alginate in 0.9 grams of glycerol as a reactive hydrogel precursor, 2 grams of tetracalcium phosphate (TTCP) as an incomplete portion of a self-hardening (TTCP+DCPA) calcium phosphate cement filler system, and 0.5 grams calcium chloride to cause alginate hardening. The aqueous paste contained 0.5 grams of polyacrylic acid (PAAc) (Aldrich Chemical Company, Inc., Milwaukee, Wis.) dissolved in 0.5 grams of water as a reactive hydrogel and 1 gram DCPA as the other portion of the calcium phosphate cement filler system. The two pastes were combined, whereupon the PAAc gel hardened due to the alkalinity of TTCP and the calcium from both TTCP and DCPA. Additionally, sodium alginate dissolved in water and formed a hardened gel by cross linking with the calcium from the calcium chloride. The material set after about 15 minutes. The sample was allowed to fully set by placing it into water at 37° C. for an additional 24 hours and was then subjected to a dye penetration test as described above. Although dye appeared to have completely penetrated into the sample, the intensity of the dye was extremely low.

Example 25

In this Example, the non-aqueous paste contained 0.25 grams of polyvinyl butyral (PVB) in 0.75 grams of ethanol as a non-reactive hydrogel precursor and 3 grams of Portland cement as a self-hardening filler system. The aqueous paste contained 0.05 grams of sodium polyvinyl alcohol (PVA) in 0.45 grams of water as a non-reactive hydrogel and 1.5 grams of FA as a non-hardening filler. Once the two pastes were combined, the water allowed the Portland cement to harden in 10 min. The sample was allowed to fully set by placing it in water at 37° C. for an additional 24 hours and was then subjected to a dye penetration test as described above. Dye penetration into the sample was 0.38 mm±0.17 mm (mean±s.d.; n=6).

Example 26

In this Example, the non-aqueous pastes contained 0.25 grams of PVB in 0.75 grams of absolute ethanol as a non-reactive hydrogel precursor and tetracalcium phosphate (TTCP) as an incomplete portion of a self-hardening (TTCP+DCPA) calcium phosphate cement filler system. The aqueous paste contained 0.05 grams of PVA dissolved in 0.45 grams of water as a non-reactive hydrogel and 1 gram of dicalcium phosphate anhydrous (DCPA) as the other portion of the calcium phosphate cement filler system. Once the two pastes were combined, the paste hardened in about 5 min. TTCP and DCPA reacted to form hardened cement with hydroxyapatite as the product. The sample was allowed to fully set by placing it into water at 37° C. for an additional 24 hours and was then subjected to a dye penetration test as described above. Dye penetration into the sample was 0.27 mm±0.18 mm (mean±s.d.; n=6).

Example 27

In this Example, the non-aqueous paste contained 0.25 grams of PVB in 0.75 grams of absolute ethanol as a non-reactive hydrogel precursor and 2 grams of Portland cement as a self-hardening filler system. The aqueous paste contained 0.15 grams of chitosan malate in 0.85 grams of water as a reactive hydrogel and 1.5 grams of FA as a non-hardening filler. Once the two pastes were combined, chitosan malate hardened due to the base from the Portland cement, and the water allowed Portland cement to harden. After 5 min, it was placed into water. The sample was allowed to fully set by placing it into water at 37° C. for an additional 24 hours and was then subjected to a dye penetration test as described above. Dye penetration into the sample was 0.46 mm±0.26 mm (mean±s.d.; n=6).

Example 28

In this Example, the non-aqueous paste contained 0.3 grams of $Ca_3SiO_5$ in 0.2 grams of glycerol. The aqueous paste contained 1 gram of DCPA in 0.5 grams of 0.5 M $Na_2HPO_4$ solution. Once the two pastes are combined, the phosphate solution allowed $Ca_3SiO_5$ and DCPA to react and harden. After 40 min, the hardened filler material was placed into water at 37° C. The sample was allowed to fully set by placing it into water at 37° C. for an additional 24 hours and was then subjected to a dye penetration test as described above. Dye penetration into the sample was 0.02 mm±0.02 mm (mean±s.d.; n=5).

Example 29

The non-aqueous paste of this Example contained 0.6 grams of $Ca_3SiO_5$ in 0.4 grams of glycerol. The aqueous paste contained 1.79 grams of DCPA in 0.93 grams of 1.5 M $NaH_2PO_4$ solution. Once the two pastes were combined, the phosphate solution allowed $Ca_3SiO_5$ and DCPA to react and harden. After 15 min, the hardened filler material was placed into water at 37° C. The sample was allowed to fully set by placing it into water at 37° C. for an additional 24 hours and was then subjected to a dye penetration test as described above. Dye penetration into the sample was 0.001 mm±0.001 mm (mean±s.d.; n=5).

Example 30

The non-aqueous paste of this Example contained 1.4 grams of tetracalcium phosphate (TTCP) as an incomplete portion of a self-hardening (TTCP+DCPA) calcium phosphate cement filler system, 0.6 grams of $Ca_3SiO_5$, and 0.2 grams of $Na_2HPO_4$, in 1.17 grams of glycerol. The aqueous paste contained 1 gram of dicalcium phosphate anhydrous (DCPA) as the other portion of the calcium phosphate cement filler system, 1.2 grams of $BaSO_4$, and 0.165 grams of chitosan lactate in 0.935 grams of water. Once the two pastes were combined, chitosan lactate formed a hardened gel within 60 min with the aid of base derived from TTCP. Additionally, the TTCP and DCPA reacted to form a hardened cement with hydroxyapatite as the product. $Na_2HPO_4$ crystals promoted the setting reaction. The filler material sample was allowed to fully set by placing it into water at 37° C. for an additional 24 hours and was then subjected to a dye penetration test as described above. Dye penetration into the sample was 0.05 mm±0.02 mm (mean±s.d.; n=5).

Example 31

In this Example, the non-aqueous paste contained 1.5 grams of a self-hardening calcium phosphate cement filler system and 0.5 grams of $Ca_3SiO_5$ in 1.2 grams of glycerol. The aqueous paste contained 0.75 grams of monocalcium phosphate monohydrate (MCPM), 0.75 grams $BaSO_4$, 0.1 grams of chitosan lactate, and 0.11 grams of glycerol in 0.9 grams of water. Once the two pastes were combined, chitosan lactate formed a hardened gel within 10 min with the aid of base derived from $Ca_3SiO_5$. Additionally, the TTCP and DCPA reacted to form hardened cement with hydroxyapatite as the product. The filler material sample was allowed to fully set by placing it into water at 37° C. for an additional 24 hours and was then subjected to a dye penetration test as described above. Dye penetration into the sample was 0.04 mm±0.03 mm (mean±s.d.; n=5).

Example 32

In this Example, the non-aqueous paste contained 3 grams of Portland cement in 1.2 grams of glycerol. The aqueous paste contained 2 grams of MCPM and 0.1 grams of glycerol in 1gram of 8.5 M glycolic acid solution. Once the two pastes were combined, the water allowed the Portland cement to harden. The filler material hardened at 9.3 min±0.6 min (mean±s.d.; n=3). The sample was allowed to fully set by placing it into water at 37° C. for an additional 24 hours and was then subjected to a dye penetration test as described above. Dye penetration into the sample was 0.001 mm±0.001 mm (mean±s.d.; n=5).

Example 33

The non-aqueous paste of this Example contained 0.6 grams of $Ca_3SiO_5$ in 0.4 grams of glycerol. The aqueous paste contained 1.2 grams of MCPM in 0.5 grams of 8.5 M glycolic acid solution. Once the two pastes were combined, MCPM reacted with $Ca_3SiO_5$, and also glycolic acid formed a calcium salt, which hardened. After 10 min, the hardened filler material was placed into water at 37° C. The sample was allowed to fully set by placing it into water at 37° C. for an additional 24 hours and was then subjected to a dye penetration test as described above. Dye penetration into the sample was 0.02 mm±0.02 mm (mean±s.d.; n=5).

Compositions similar to the compositions given in the following additional examples are described in copending application Ser. No. 11/550,586, entitled "DUAL-PHASE CEMENT PRECURSOR SYSTEMS FOR BONE REPAIR" and filed contemporaneously herewith.

Example 34

The non-aqueous paste contains 3 grams of Portland cement as a self-hardening filler in 1.22 grams of glycerol. The aqueous paste contains 1.508 grams of MCPM and 0.23 grams of chitosan lactate in 1.31 grams of water. Once the two pastes are combined, chitosan lactate hardens due to the base from Portland cement and the water allows Portland cement to harden. After 5 min, it was placed into water. The sample was allowed to fully set by placing it into water at 37° C. for an additional 24 hours and was then subjected to a dye penetration test as described above. Dye penetration into the sample was 0.006 mm±0.007 mm (mean±s.d.; n=5).

Example 35

Paste 1 was prepared by blending 3 g of MCPM into 1.35 g of an aqueous solution containing 0.15 g of chitosan lactate. Paste 2 was composed of 3 g of a calcium phosphate cement (CPC) mixture (containing 73 wt % TTCP and 27 wt % DCPA) and 1.2 g of glycerin. The combined pastes hardened in 5.7 min±1.2 min (mean±s.d.; n=3), and was placed in water at 37° C. The sample was allowed to fully set by placing it into water at 37° C. for an additional 24 hours and was then subjected to a dye penetration test as described above. Dye penetration into the sample was 0.03 mm±0.03 mm (mean±s.d.; n=5).

Example 36

Paste 1 was prepared by blending 3 g of MCPM into two liquids, the first liquid being 4.8 g of an aqueous solution containing 8.5M glycolic acid and 10 wt % chitosan lactate, and the second liquid being 2 g of glycerin. Paste 2 was composed of 3 g of a calcium phosphate cement (CPC) mixture (containing 73 wt % TTCP and 27 wt % DCPA) and 1.2 g of glycerin. Once the two pastes were combined, chitosan lactate hardened due to the base from the CPC, and the water allowed CPC to harden. Also, glycolic acid reacted with calcium from CPC to form a calcium salt. After 10 min, the sample was placed into water at 37° C. The sample was allowed to fully set by placing it into water at 37° C. for an additional 24 hours and was then subjected to a dye penetration test as described above. Dye penetration into the sample was 0.02 mm±0.02 mm (mean±s.d.; n=5).

Example 37

The non-aqueous paste contains 3 grams of Portland cement in 1.2 grams of glycerol. The aqueous paste contains 3 grams of MCPM and 0.4 grams of chitosan lactate in 3.6 grams of 8.5 M glycolic acid. Once the two pastes are combined, chitosan lactate hardens due to the base from Portland cement and the water allows Portland cement to harden. Also glycolic acid reacts with Ca from CPC to form Ca-salt. After 5 min, it was placed into water at 37° C. The sample was allowed to fully set by placing it into water at 37° C. for an additional 24 hours and was then subjected to a dye penetration test as described above. Dye penetration into the sample was 0.05 mm±0.04 mm (mean±s.d.; n=5).

Example 38

The non-aqueous paste contains 3.01 grams of Portland cement in 1.22 grams of glycerol. The aqueous paste contains 3 grams of MCPM, 0.017 grams of HPMC, and 0.5 grams of glycerol in 1.5 grams MCPM-DCPD saturated solution. Once the two pastes are combined, the water allows Portland cement to harden. Also MCPM reacts with Portland cement to form hydroxyapatite. After 5 min, it was placed into water at 37° C. The sample was allowed to fully set by placing it into water at 37° C. for an additional 24 hours and was then subjected to a dye penetration test as described above. Dye penetration into the sample was 0.04 mm±0.05 mm (mean s.d.; n=5).

It is thus seen that, in certain embodiments, the invention provides a root canal filling material. In other embodiments, endodontic methods are provided.

All references, including publications, patent applications, and patents, cited herein are hereby incorporated by reference. In any listing of possible ingredients or components, mixtures of the possible ingredients or components are contemplated unless expressly indicated otherwise. The description of certain embodiments as "preferred" embodiments, and other recitation of embodiments, features, or ranges as being preferred, is not deemed to be limiting, and the invention is deemed to encompass embodiments that are presently deemed to be less preferred. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The description herein of any reference or patent is not intended to constitute a concession that such reference is available as prior art against the present invention.

The invention claimed is:

1. A hydrophilic, water-setting, endodontic, premixed root canal filling paste mixture for filling a root canal in vivo, comprising:
   (1) a matrix consisting essentially of a first biocompatible, stable, non-toxic, paste phase, said paste phase consisting essentially of hydrogel former polymer in a non-aqueous liquid carrier, said carrier selected from the group consisting of glycerol, propyl alcohol and absolute ethanol, said hydrogel former polymer selected from the group consisting of polyvinyl acetate, polyvinyl butyral and polyvinyl esters and characterized as forming a hardened mass as a seal in the presence of water; and
   (2) a filler second phase of particles, said particles selected from the group consisting of calcium phosphate compounds, mineral trioxide aggregates and Portland cement, characterized as non-reactive with said hydrogel former polymers;
   said first and second phases in combination consisting essentially of a substantially non-aqueous, premixed paste mixture characterized as capable of storage as a stable root canal filling and sealing paste mixture in a container without hardening and without forming a hydrogel polymeric mass prior to in situ dispensation as an endodontic root canal filling mixture and further characterized as forming a hardened polymeric mass in situ in an aqueous environment formed substantially by said hydrogel former polymer, said non-aqueous liquid carrier comprising at least about 17% by weight of said paste mixture to about 53% by weight of said paste mixture and said filler particles comprising at least 26% by weight of said paste mixture to about 80% by weight of said paste mixture and the balance at least one of said polymers, the ratio of the filler particles to the hydrogel former polymer at least greater than about 3.0.

2. A root canal filling mixture according to claim 1, wherein said root canal filling mixture further comprises a radio opaque filler.

3. A root canal filling mixture according to claim 1, wherein said root canal filling mixture further comprises an antibacterial agent.

4. A root canal filling mixture according to claim 1 characterized as capable of forming a hydrogel polymer mass having a satisfactory hardness in situ as a root canal filling and sealing mixture in at least 24 hours and capable of storage prior to in vivo filling without hardening for at least seven days.

* * * * *

UNITED STATES PATENT AND TRADEMARK OFFICE
CERTIFICATE OF CORRECTION

PATENT NO. : 9,101,436 B2
APPLICATION NO. : 11/550543
DATED : August 11, 2015
INVENTOR(S) : Laurence C. Chow et al.

It is certified that error appears in the above-identified patent and that said Letters Patent is hereby corrected as shown below:

Specification

Change column 13, lines 29 - 31 to read "The aqueous paste contained 2 grams of MCPM and 0.1 grams of glycerol in 1 gram of 8.5M glycolic acid solution."

Signed and Sealed this
Eighth Day of November, 2016

Michelle K. Lee
*Director of the United States Patent and Trademark Office*

UNITED STATES PATENT AND TRADEMARK OFFICE
CERTIFICATE OF CORRECTION

PATENT NO. : 9,101,436 B2
APPLICATION NO. : 11/550543
DATED : August 11, 2015
INVENTOR(S) : Laurence C. Chow et al.

Page 1 of 1

It is certified that error appears in the above-identified patent and that said Letters Patent is hereby corrected as shown below:

In the Specification

The following should replace the paragraph at Column 1, Lines 24 - 28:
This invention was made with government support under grant R01 DE011789 awarded by the National Institutes of Health. The government has certain rights in the invention.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*